United States Patent
Janson et al.

(10) Patent No.: US 12,370,377 B2
(45) Date of Patent: Jul. 29, 2025

(54) GENERATING A PLURALITY OF POTENTIAL TREATMENT PLANS FOR MULTI-CRITERIA OPTIMIZATION

(71) Applicant: RaySearch Laboratories AB (Publ), Stockholm (SE)

(72) Inventors: Martin Janson, Enskededalen (SE); Rasmus Bokrantz, Enebyberg (SE)

(73) Assignee: Raysearch Laboratories AB (publ), Stockholm (SE)

( * ) Notice: Subject to any disclaimer, the term of this patent is extended or adjusted under 35 U.S.C. 154(b) by 242 days.

(21) Appl. No.: 17/760,326

(22) PCT Filed: Feb. 10, 2021

(86) PCT No.: PCT/EP2021/053203
§ 371 (c)(1),
(2) Date: Aug. 8, 2022

(87) PCT Pub. No.: WO2021/165118
PCT Pub. Date: Aug. 26, 2021

(65) Prior Publication Data
US 2023/0076214 A1 Mar. 9, 2023

(30) Foreign Application Priority Data
Feb. 21, 2020 (EP) .................. 20158795

(51) Int. Cl.
*A61N 5/10* (2006.01)
*G16H 20/40* (2018.01)

(52) U.S. Cl.
CPC ........... *A61N 5/1031* (2013.01); *G16H 20/40* (2018.01)

(58) Field of Classification Search
CPC .................. A61N 5/1031; G16H 20/40
See application file for complete search history.

(56) References Cited

U.S. PATENT DOCUMENTS

| | | | |
|---|---|---|---|
| 2018/0211725 A1* | 7/2018 | Purdie | .......... G16H 10/60 |
| 2022/0040501 A1* | 2/2022 | Traneus | ........... A61N 5/1064 |

FOREIGN PATENT DOCUMENTS

| | | |
|---|---|---|
| CN | 109923615 A | 6/2019 |
| CN | 110582325 A | 12/2019 |

OTHER PUBLICATIONS

Baumann et al., Radiation oncology in the era of precision medicine, 16 Nature Reviews Cancer 234-249 (Year: 2016).*

(Continued)

*Primary Examiner* — Jordan L Jackson
(74) *Attorney, Agent, or Firm* — Noréns Patentbyrå AB

(57) ABSTRACT

It is provided a method for generating a plurality of potential treatment plans, each treatment plan specifying a distribution of radiation to a target volume, the method being performed by a treatment planning system and comprising the steps of: generating a plurality of potential treatment plans (12), for performing multi-criteria optimization (MCO), based on a set of optimization functions. At least one optimization function depends on the distribution of the product of radiation dose and linear energy transfer, LET, in a specified region of the patient, yielding a plurality of treatment plans.

10 Claims, 2 Drawing Sheets

(56) References Cited

OTHER PUBLICATIONS

Grassberger et al., Variations in linear energy transfer within clinical proton therapy fields and the potential for biological treatment planning, 80(5) Int J Radiat Oncol Biol Phys. 1559-1566 (Year: 2010).*
Giantsoudi et al., Linear Energy Transfer-Guided Optimization in Intensity Modulated Proton Therapy: Feasibility Study and Clinical Potential, 87(1) Int J of Radiation Oncology*Biology*Physics 216-222 (Sep. 2013) (Year: 2013).*
Giantsoudi Drosoula et al., "Linear Energy Transfer-Guiden Optimization in Intensity Modulated Proton Therapy: Feasibility Study and Clinical Potential", International Journal of Radiation: Oncology Biologigal Physics, Pergamon Press, USA, vol. 87, No. 1, Jun. 19, 2013.
Paganetti Harald et al., "Relative Biological Effectiveness Uncertainties and Implications for Beam Arrangements and Dose Constraints in Proton Therapy", Seminars in Radiation Oncology, vol. 28, No. 3, Jul. 1, 2018.
Wenhua Cao et al., "Linear energy transfer incorporated intensity modulated proton therapy optimization", Physics in Medicine and Biology, Institute of Physics Publishing, Bristol Great Britain, vol. 63, No. 1, Dec. 19, 2017.
First Office Action dated Aug. 31, 2024 in corresponding Chinese patent application, Chinese Patent Office, Beijing, China.

* cited by examiner

GENERATING A PLURALITY OF POTENTIAL TREATMENT PLANS FOR MULTI-CRITERIA OPTIMIZATION

TECHNICAL FIELD

The present disclosure relates to the field of treatment plans for distribution of radiation to a target volume and in particular to multi-criteria optimization in this context.

BACKGROUND

In ion beam therapy, a beam of ions (e.g. protons or heavier ions) is directed towards a target volume. The target volume can e.g. represent a cancer tumor. The particles penetrate the tissue and deliver a dose of energy to induce cell death. An advantage of ion beam therapy is that there is a significant peak in the dose distribution, known as a Bragg peak. The Bragg peak is a peak of dose delivery occurring at a certain depth, after which the dose delivery falls of quickly. This can be compared with electron beam therapy or X-ray (photon) therapy where the maximum dose always occurs at shallow depth and distal dose fall-off cannot be controlled with the same sharp fall-off as for ion therapy.

The depth of the Bragg peak in the patient can be controlled by adjusting the kinetic energy of the particles. Lateral position can be controlled using electromagnets to deflect the focused beam. This allows for delivery of highly localized doses at well-controlled positions in the patient. The dose delivered from a certain combination of kinetic energy, and lateral deflection of the beam is referred to as a spot. The number of particles delivered to a spot is commonly referred to as the spot weight. By providing spots in many different locations in a three-dimensional space, the target volume can be covered with a desired dose distribution. The kinetic energies of the spots are often, but not necessarily, distributed over a number of discrete energies. A group of spots with the same kinetic energy, but different lateral deflection is often referred to as an energy layer. This procedure is called active scanning ion beam therapy, also known as pencil beam scanning.

The planning of how the spots should be delivered is performed in a treatment planning system, resulting in a treatment plan. The treatment planning system determines the energy layers to be used and the distribution and weights of spots therein, but the treatment planning system does not deliver the ion beam. The delivery of the ion beam is done by a radiation delivery system, to which the treatment plan is provided.

The determination of the treatment plan can be done in many different ways. One way is to use Multi-Criteria Optimization (MCO). In MCO, multiple potential treatment plans are generated, each of which is optimized in a different way. The planning operator can then linearly combine these potential treatment plans in real-time, where the combination is generated and visualized in real-time, along with performance indicators.

Giantsoudi Drosoula et al have published: "Linear Energy Transfer-Guided Optimization in Intensity Modulated Proton Therapy: Feasibility Study and Clinical Potential", INTERNATIONAL JOURNAL OF RADIATION: ONCOLOGY BIOLOGY PHYSICS, PERGAMON PRESS, USA, vol. 87, no. 1, 19 Jun. 2013, pages 216-222. However, any improvement in how the treatment plans are generated is of great benefit.

SUMMARY

One objective is to improve how optimization is how to improve MCO in relation to Relative Biological Effectiveness (RBE).

According to a first aspect, it is provided a method for generating a plurality of potential treatment plans, each treatment plan specifying a distribution of radiation to a target volume, the method being performed by a treatment planning system and comprising the steps of: generating a plurality of potential treatment plans (12), for multi-criteria optimization (MCO), based on a set of optimization functions. At least one optimization function depends on the distribution of the product of radiation dose and linear energy transfer, LET, in a specified region of the patient, yielding a plurality of treatment plans.

The at least one optimization function may be specified as an objective.

The objective may be to minimize or maximize the at least one optimization function value.

The at least one optimization function may be specified as a constraint.

The constraint may be that the at least one optimization function value may not exceed a specified value or that the at least one optimization function value may not be lower than a specified value.

The method may further comprise the step of: providing the plurality of treatment plans to an MCO module.

According to a second aspect, it is provided a treatment planning system for generating a plurality of potential treatment plans, each treatment plan specifying a distribution of radiation to a target volume. The treatment planning system comprises: a processor; and a memory storing instructions that, when executed by the processor, cause the treatment planning system to: generate a plurality of potential treatment plans (12), for multi-criteria optimization (MCO), based on a set of optimization functions, where at least one optimization function depends on the distribution of the product of radiation dose and linear energy transfer, LET, in a specified region of the patient, yielding a plurality of treatment plans.

The at least one optimization function may be specified as an objective.

The objective may be to minimize or maximize the at least one optimization function value.

The at least one optimization function may be specified as a constraint.

The constraint may be that the at least one optimization function value may not exceed a specified value or that the at least one optimization function value may not be lower than a specified value.

According to a third aspect, it is provided a computer program for generating a plurality of potential treatment plans, each treatment plan specifying a distribution of radiation to a target volume. The computer program comprises computer program code which, when run on a treatment planning system causes the treatment planning system to: perform multi-criteria optimization based on a set of optimization functions, where at least one optimization function depends on the distribution of the product of radiation dose and linear energy transfer, LET, in a specified region of the patient, yielding a plurality of treatment plans.

According to a fourth aspect, it is provided a computer program product comprising a computer program according to the third aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

Aspects and embodiments are now described, by way of example, with reference to the accompanying drawings, in which.

DETAILED DESCRIPTION

The aspects of the present disclosure will now be described more fully hereinafter with reference to the accompanying drawings, in which certain embodiments of the invention are shown. These aspects may, however, be embodied in many different forms and should not be construed as limiting; rather, these embodiments are provided by way of example so that this disclosure will be thorough and complete, and to fully convey the scope of all aspects of invention to those skilled in the art. Like numbers refer to like elements throughout the description.

Figure 1:
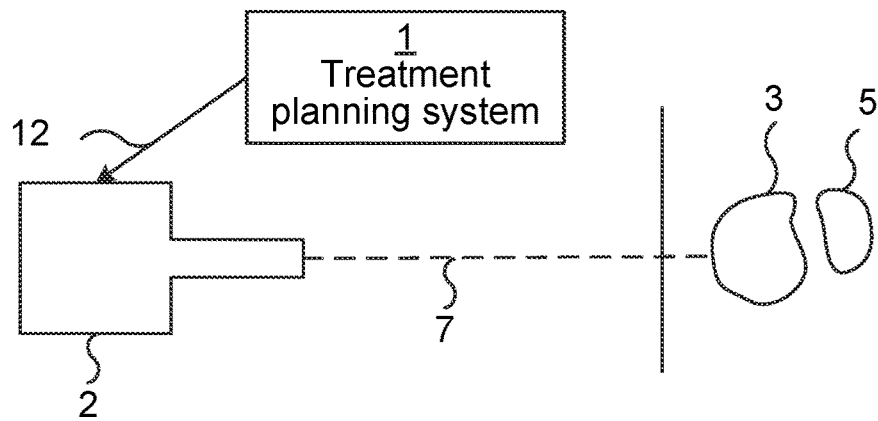
FIG. 1 is a schematic drawing illustrating an environment in which embodiments presented herein can be applied.

FIG. 1 is a schematic drawing illustrating an environment in which embodiments presented herein can be applied. A treatment planning system 1 determines a distribution radiation for radiation therapy. This is communicated as a treatment plan 12 to a radiation delivery system 2. Based on the treatment plan, the radiation delivery system 2 generates a beam 7 for providing radiation to a target volume 3 of a patient, while avoiding radiation to an organ at risk 5.

The radiation delivery system 2 can e.g. be an ion beam system for pencil beam scanning. In such a case, radiation is provided in a large number of spots, wherein each spot has a position in a three-dimensional co-ordinate system. The location of the dose maximum (Bragg peak) of the spot depth-wise, i.e. along the z-axis, is controlled by the kinetic energy of the ions; higher energy results in a deeper location of the dose maximum. Moreover, the lateral position is controlled using electromagnets to deflect the beam 7. In this way, a dose distribution covering the target volume 3 in three dimensions can be achieved while radiation to the organ at risk 5 is kept low.

Alternatively, the radiation delivery system 2 is based on tomotherapy, where radiation is delivered during circular or helical movement around the patient.

Other types of radiation delivery systems are also possible.

Figure 2:
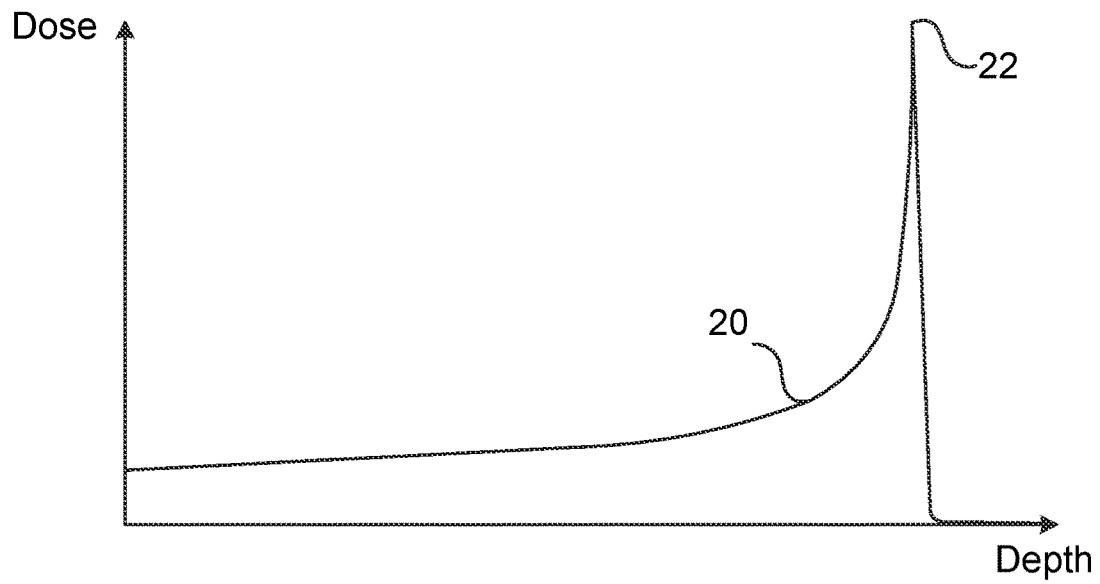
FIG. 2 is a schematic graph illustrating the dose delivery using ions, and in particular the Bragg peak using the radiation delivery system of FIG. 1.

FIG. 2 is a schematic graph illustrating the dose delivery using ions, and in particular the Bragg peak using the radiation delivery system 2 of FIG. 1. The horizontal axis represents depth in water and the vertical axis represents dose. A curve 20 shows dose distribution of the dose in relation to the depth. The Bragg peak 22 is the peak of the curve, which appears just prior to the dose dropping off.

When radiation is delivered to a patient, ions result in different biological effects in terms of destroyed cells compared to photons of the same amount of absorbed dose (measured in Gray). To be able to compare dose levels from ion radiation to dose levels of photon radiation, ion dose is often transformed to a photon dose distribution that would give the equivalent biological effect in the patient. The ratio between this photon equivalent dose and the physical absorbed dose from the ion radiation is referred to as the Relative Biological Effectiveness (RBE). The transformation between physically absorbed dose and photon equivalent dose is thus performed using an RBE model. There are several RBE models available, from the simplest one that is just a constant scaling factor to the very complex ones that depend on e.g. ion type, ion energy, and target elemental composition.

The most common RBE model used for light ion therapy is the constant factor model, where e.g. RBE=1.1 is commonly used for protons. However, it is well known that the RBE can be substantially higher in parts of dose distribution, leading to unwanted effects. It has been found that high Linear Energy Transfer (LET), which is the distance derivative of absorbed dose (i.e. the derivative of the curve 20 in FIG. 2), has a strong correlation with high RBE for ion beam therapy. Due to this effect, it is desirable to control the distribution of LET in the patient, when a constant factor RBE model is used.

According to embodiments presented herein, multi-criteria optimization (MCO) is performed where an optimization function depends on the distribution of the product of radiation dose and LET (herein denoted D×LET) in a specified region of the patient, or where an optimization function uses an alternative RBE model as compared to the RBE model used for the other objectives and/or constraints of the MCO problems. This is described in more detail below.

Figure 3:
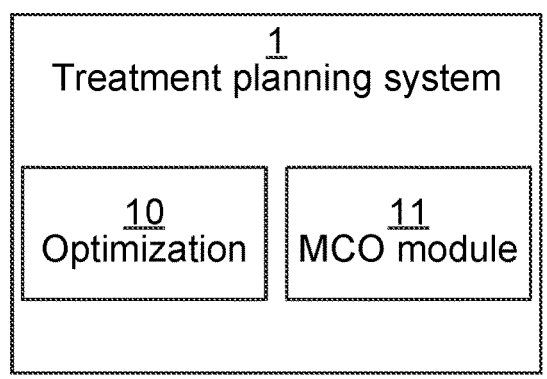
FIG. 3 is a schematic diagram illustrating functional modules of the treatment planning system of FIG. 1.

FIG. 3 is a schematic diagram illustrating functional modules of the treatment planning system of FIG. 1. The modules are implemented using software instructions such as a computer program executing in the treatment planning system 1. Alternatively or additionally, the modules are implemented using hardware, such as any one or more of an ASIC (Application Specific Integrated Circuit), an FPGA (Field Programmable Gate Array), or discrete logical circuits.

An optimization module 10 is the module that performs optimizations to arrive at a potential treatment plan. As explained in more detail below, several different treatment plans can be determined by the optimization module 10 for multi-criteria optimization (MCO). Each treatment plan is optimized based on one or more optimization functions. Each treatment plan can be limited by a constraint, defining that an optimization function needs to have a value above a certain level or below a certain level. Alternatively or additionally, each treatment plan has an objective, which defines that an optimization function needs to have a value as high as possible or as low as possible.

The optimization module outputs multiple treatment plans, each of which is optimized based on a certain set of one or more optimization functions as constraints and/or objectives. The multiple plans include single objective plans, which are optimized for a single optimization function. Moreover, the multiple plans can contain additional plans where multiple optimization functions are combined.

Since many optimization functions conflict with each other, an MCO module 11 is used to find a balance between the optimization functions. The MCO module 11 allows a planning operator (i.e. a user of the treatment planning system) to generate a navigated treatment plan based on the multiple treatment plans using Multi-Criteria Optimization. The planning operator can freely adjust the priority of any one or more of the treatment plans. When an adjustment of a treatment plan is done, e.g. using slider controls in a Graphical User Interface (GUI), a navigated treatment plan is regenerated as a concave linear combination of the multiple treatment plans.

Several performance indicators of the navigated treatment plan are calculated and presented to the planning operator in real-time. The performance indicators can include a graphical representation of dose distribution (in 2D and/or 3D) and numerical values, as well as binary indicators, e.g. of whether specific clinical targets are fulfilled or not.

This allows the planning operator to adjust the weight of the different potential treatment plans and evaluate the different treatment plans in real-time. When the planning operator is satisfied with the performance indicators, the navigated treatment plan is used as the base for treatment by the radiation delivery system.

Figure 4:
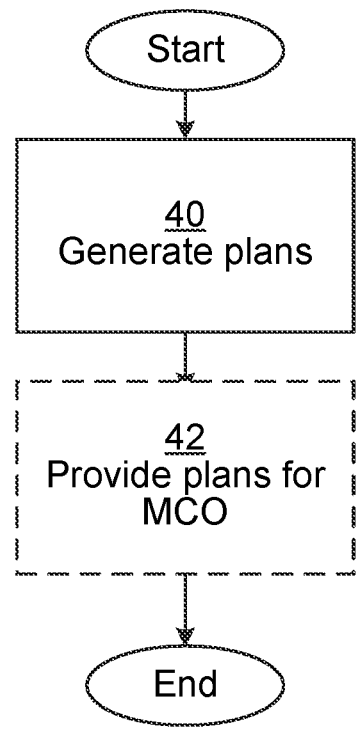
FIG. 4 is a flow chart illustrating embodiments of a method for generating a plurality of potential treatment plans, the method being performed in the treatment planning system of FIG. 1.

FIG. 4 is a flow chart illustrating embodiments of a method for generating a plurality of potential treatment plans, the method being performed in the treatment planning system of FIG. 1. Each treatment plan specifies a distribution of radiation to a target volume. The method can be performed in the optimization module 10 of the treatment planning system 1.

In a generate plans step 40, the treatment planning system generates a plurality of potential plans. The plurality of plans are intended to be used for MCO (as described above). The plurality of plans are generated based on a set of optimization functions. At least one optimization function depends on the distribution of the product of radiation dose and LET (D×LET) in a specified region of the patient. The result of this step is the plurality of treatment plans.

The specified region can be any suitable region defined in three dimensions, e.g. the target volume, an organ at risk, any subregion of these, etc.

The optimizations are based on the set of optimization functions by iteratively adjusting a set of optimization variables. The configuration of the optimization variables determines the values of the optimization functions.

In one embodiment, the at least one optimization function is specified as an objective. The objective can be to minimize or maximize the at least one optimization function value.

In one embodiment, the at least one optimization function is specified as a constraint. For instance, the constraint can be that the at least one optimization function value may not exceed a specified value or that the at least one optimization function value may not be lower than a specified value.

In an optional provide treatment plans for MCO step 42, after the optimization is done, the treatment plans are provided to the MCO module 11, at which point the planning operator can navigate the plans as described above. In other words, step 40 corresponds to an optimization stage to generate a plurality of plans (optimized at least partly on D×LET), which are provided for the MCO module in this step (step 42). These plans can then be linearly combined in real-time by an operator of the MCO module.

By including an optimization function based on D×LET distribution, already the optimizations are performed to optimize based on the D×LET. This greatly improves the plans in relation to RBE, since the D×LET distribution is closely related to RBE.

Figure 5:
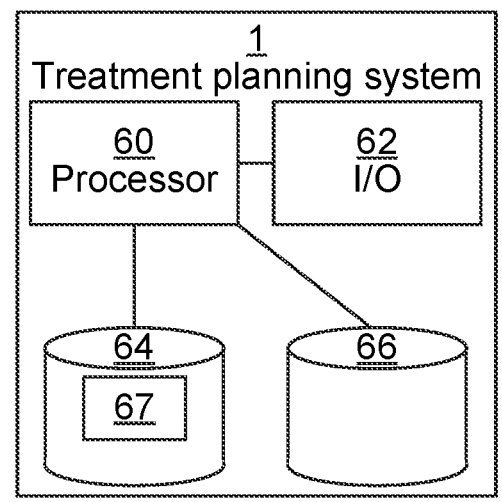
FIG. 5 is a schematic diagram illustrating components of the treatment planning system of FIG. 1 according to one embodiment.

FIG. 5 is a schematic diagram illustrating components of the treatment planning system 1 of FIG. 1 according to one embodiment. A processor 60 is provided using any combination of one or more of a suitable central processing unit (CPU), multiprocessor, microcontroller, digital signal processor (DSP), application specific integrated circuit etc., capable of executing software instructions 67 stored in a memory 64, which can thus be a computer program product. The processor 60 can be configured to execute the method described with reference to FIG. 4 above.

The memory 64 can be any combination of random-access memory (RAM) and read-only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60.

The treatment planning system 1 further comprises an I/O interface 62 for communicating with external entities. Optionally, the I/O interface 62 also includes a user interface.

Other components of the treatment planning system 1 are omitted in order not to obscure the concepts presented herein.

Figure 6:
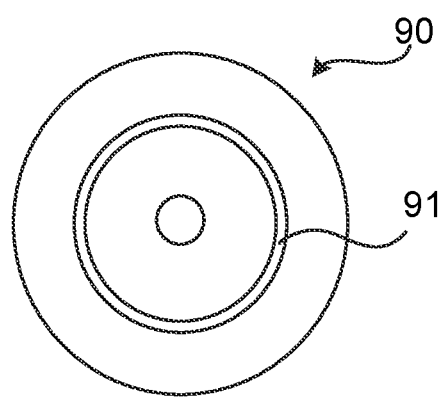
FIG. 6 shows one example of a computer program product comprising computer readable means.

FIG. 6 shows one example of a computer program product comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 5. While the computer program 91 is here schematically shown as a track on the depicted optical disk, the computer program can be stored in any way which is suitable for the computer program product, such as a removable solid-state memory, e.g. a Universal Serial Bus (USB) drive.

Here now follows a set embodiments with roman numerals.

i. A method for checking quality of a treatment plan, wherein a treatment plan specifies a distribution of radiation to thereby provide radiation to a planning target volume, the method being performed by a quality assurance device and comprising the steps of:

obtaining a treatment plan and a corresponding first dose, the treatment plan having been calculated in a treatment planning system, the first dose being a predicted dose to be deposited in the patient using the treatment plan;

initiating a calculation of a secondary dose, being a dose deposited by the treatment plan, using a secondary dose calculation algorithm;

repeatedly calculating a confidence interval of a comparative statistical measurement by comparing the first dose and the secondary dose over a defined geometric volume; and interrupting the calculation of the secondary dose when the confidence interval is better than at least one predefined criterion, in which case the treatment plan is considered to pass quality assurance.

ii. The method according to embodiment i, wherein each voxel in the secondary dose comprises estimates of a current confidence interval for the voxel.

iii. The method according to embodiment i or ii, wherein the defined geometric volume is the planning target volume.

iv. The method according to embodiment i or ii, wherein the defined geometric volume is an organ at risk.

v. The method according to embodiment i or ii, wherein the defined geometric volume covers the planning target volume and an organ at risk.

vi. The method according to any one of the preceding embodiments, wherein the step of calculating the confidence interval of the comparative statistical measurement is based on available confidence intervals for voxels in the secondary dose, and on a spread of possible secondary dose.

vii. The method according to embodiment vi, wherein the comparative statistical measurement is based on calculating a similarity by accumulating difference measurements between corresponding voxels in the first dose and the second dose.

viii. The method according to embodiment vi, wherein the comparative statistical measurement is based on calculating a similarity by finding a difference between a third value and a fourth value, wherein the third value is obtained by accumulating dose values of the first dose in all voxels in the defined geometric volume, and the fourth value is obtained by accumulating dose values of the second dose in all voxels of the defined geometric volume.

ix. A quality assurance device for checking quality of a treatment plan, wherein a treatment plan specifies a distribution of radiation to thereby provide radiation to a planning target volume, the quality assurance device comprising:

a processor; and a memory storing instructions that, when executed by the processor, cause the quality assurance device to:

obtain a treatment plan and a corresponding first dose, the treatment plan having been calculated in a treatment planning system, the first dose being a predicted dose to be deposited in the patient using the treatment plan;

initiate a calculation of a secondary dose, being a dose deposited by the treatment plan, using a secondary dose calculation algorithm;

repeatedly calculate a confidence interval of a comparative statistical measurement by comparing the first dose and the secondary dose over a defined geometric volume; and interrupt the calculation of the secondary dose when the confidence interval is better than at least one predefined criterion, in which case the treatment plan is considered to pass quality assurance.

x. The quality assurance device according to embodiment ix, wherein each voxel in the secondary dose comprises estimates of a current confidence interval for the voxel.

xi. The quality assurance device according to embodiment ix or x, wherein the defined geometric volume is the planning target volume.

xii. The quality assurance device according to embodiment ix or x, wherein the defined geometric volume is an organ at risk.

xiii. The quality assurance device according to embodiment ix or x, wherein the defined geometric volume covers the planning target volume and an organ at risk.

xiv. A computer program for checking quality of a treatment plan, wherein a treatment plan specifies a distribution of radiation to thereby provide radiation to a planning target volume, the computer program comprising computer program code which, when run on a quality assurance device causes the quality assurance device to:

obtain a treatment plan and a corresponding first dose, the treatment plan having been calculated in a treatment planning system, the first dose being a predicted dose to be deposited in the patient using the treatment plan;

initiate a calculation of a secondary dose, being a dose deposited by the treatment plan, using a secondary dose calculation algorithm;

repeatedly calculate a confidence interval of a comparative statistical measurement by comparing the first dose and the secondary dose over a defined geometric volume; and interrupt the calculation of the secondary dose when the confidence interval is better than at least one predefined criterion, in which case the treatment plan is considered to pass quality assurance.

xv. A computer program product comprising a computer program according to embodiment xiv and a computer readable means on which the computer program is stored.

The aspects of the present disclosure have mainly been described above with reference to a few embodiments. However, as is readily appreciated by a person skilled in the art, other embodiments than the ones disclosed above are equally possible within the scope of the invention, as defined by the appended patent claims. Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method for generating a plurality of potential treatment plans to improve ion beam therapy precision, the method being performed by a treatment planning system, comprising:

obtaining patient-specific imaging data to determine anatomical structures and tissue density variations;

generating a plurality of treatment plans configured to dynamically adjust beam energy levels and angles of a radiation delivery system, based on the anatomical structures and tissue density variations in the patient-specific imaging data, wherein each treatment plan specifies a distribution of radiation to a target volume and the generation includes applying a set of optimization functions, wherein at least one optimization function depends on the distribution of the product of radiation dose and linear energy transfer in a specified region of the patient;

executing, using a processor of the treatment planning system, specific algorithms for calculating the optimization functions and incorporating the distribution of the product of radiation dose and the linear energy transfer to enhance the accuracy of the radiation therapy delivery;

providing the plurality of treatment plans to a Multi-Criteria Optimization module;

generating, by the Multi-Criteria Optimization module, a navigated treatment plan by real-time-adjustment and evaluation of the treatment plans based on clinical performance indicators, including at least one of: dose distribution and clinical targets; and delivering ion beam therapy to the patient by the radiation delivery system using the navigated treatment plan.

2. The method of claim 1, wherein the at least one optimization function is specified as an objective.

3. The method of claim 2, wherein the objective is to minimize or maximize the at least one optimization function value.

4. The method of claim 1, wherein the at least one optimization function is specified as a constraint.

5. The method of claim 4, wherein the constraint is that the at least one optimization function value may not exceed a specified value or that the at least one optimization function value may not be lower than a specified value.

6. A treatment planning system for generating a plurality of potential treatment plans to improve ion beam therapy precision, the treatment planning system comprising:

a radiation delivery system;

a processor; and a memory storing instructions that, when executed by the processor, cause the treatment planning system to:

obtain patient-specific imaging data to determine anatomical structures and tissue density variations;

generate a plurality of treatment plans configured to dynamically adjust beam energy levels and angles of the radiation delivery system, based on the anatomical structures and tissue density variations in the patient-specific imaging data, wherein each treatment plan specifies a distribution of radiation to a target volume and the generation includes applying a set of optimization functions, where at least one optimization function depends on the distribution of the product of radiation dose and linear energy transfer in a specified region of the patient;

execute specific algorithms for calculating the optimization functions and incorporating the distribution of the product of radiation dose and the linear energy transfer to enhance the accuracy of the radiation therapy delivery;

provide the plurality of treatment plans to a Multi-Criteria Optimization module;

generate, by the Multi-Criteria Optimization module, a navigated treatment plan by real-time adjustment and evaluation of the treatment plans based on clinical performance indicators, including at least one of: dose distribution and clinical targets; and deliver ion beam therapy to the patient by the radiation delivery system using the navigated treatment plan.

7. The treatment planning system of claim 6, wherein the at least one optimization function is specified as an objective.

8. The treatment planning system of claim 7, wherein the objective is to minimize or maximize the at least one optimization function value.

9. The treatment planning system of claim 6, wherein the at least one optimization function is specified as a constraint.

10. The treatment planning system of claim 9, wherein the constraint is that the at least one optimization function value may not exceed a specified value or that the at least one optimization function value may not be lower than a specified value.

* * * * *